(12) United States Patent
Tong

(10) Patent No.: US 7,632,671 B2
(45) Date of Patent: Dec. 15, 2009

(54) MOLECULAR DETECTION AND ASSAY BY ELECTROBIOCHIP MICRO-ARRAY

(76) Inventor: Sun-Wing Tong, 1519 Frish Moss Ct., Bakersfield, CA (US) 93311

( * ) Notice: Subject to any disclaimer, the term of this patent is extended or adjusted under 35 U.S.C. 154(b) by 427 days.

(21) Appl. No.: 10/967,592

(22) Filed: Oct. 18, 2004

(65) Prior Publication Data
US 2005/0053996 A1 Mar. 10, 2005

Related U.S. Application Data

(63) Continuation-in-part of application No. 10/846,770, filed on May 13, 2004, now abandoned, which is a continuation-in-part of application No. 09/997,059, filed on Nov. 29, 2001, now abandoned.

(30) Foreign Application Priority Data

| Dec. 20, 2001 | (TW) | ............... 90131646 A |
| Nov. 29, 2002 | (CN) | ............... 02 1 52977 |
| Sep. 15, 2003 | (HK) | ............... 03106602.4 |

(51) Int. Cl.
| C12M 1/34 | (2006.01) |
| C12M 3/00 | (2006.01) |
| C12Q 1/68 | (2006.01) |
| G01N 33/53 | (2006.01) |
| G01N 15/06 | (2006.01) |

(52) U.S. Cl. .................. 435/287.1; 435/6; 435/7.1; 435/287.2; 422/68.1

(58) Field of Classification Search ............ 435/6, 435/91.1, 183, 7.1, 287.2, 283.1, 287.1; 436/94; 536/23.1, 24.3, 24.33, 25.3; 977/704, 705, 977/719, 727, 728, 729, 800; 422/68.1
See application file for complete search history.

(56) References Cited

U.S. PATENT DOCUMENTS

| 4,321,057 A | 3/1982 | Buckles |
| 5,385,707 A | 1/1995 | Miltenyi et al. |
| 5,391,272 A | 2/1995 | Daly et al. |
| 5,966,813 A | 10/1999 | Durand |
| 5,981,921 A | 11/1999 | Yablochnikov |
| 6,104,012 A | 8/2000 | Durand |
| 6,234,375 B1 | 5/2001 | Durand |
| 6,569,647 B1 | 5/2003 | Zhang et al. |
| 6,828,432 B2 | 12/2004 | Mirkin et al. |
| 2003/0207296 A1 | 11/2003 | Park et al. |
| 2003/0215825 A1 | 11/2003 | Tong |

FOREIGN PATENT DOCUMENTS

| TW | 371714 | 10/1999 |
| WO | WO95/15496 | 6/1995 |

OTHER PUBLICATIONS

Häarmä, Harri. "Particle technologies in diagnostics", Technology Review, vol. 126, pp. 1-30 (2002).
Baselt et al., "A biosensor based on Magnetoresistance technology", vol. 13, pp. 731-739 (1998).
Robert F. Service, "New Test Could Speed Bioweapon Detection" Science, vol. 295, p. 1447 (2002).
Jaw-Min Nam et al., "Nanoparticle-Based Bio-Bar Codes for the Ultrasensitive Detection of Proteins", Science, vol. 301, pp. 1884-1886 (2003).
Park, S-J, Taton, T.A, and Mirkin, C.A.. Array-Based Electrical Detection of DNA With Nanoparticle Probes, Science, vol. 295, Feb. 22, 2002.
Baselt, et al., "A biosensor based on magnetoresistance technology," Biosensors & Bioelectronics, vol. 13, p. 731-739 (1998).
Härmä, Harri, "Particle technologies in diagnostics," Technology Review, vol. 126 (2002).
U.S. Office Action for Tong Sun Wing, U.S. Appl. No. 09/997,059, filed Nov. 29, 2001, dated Jul. 17, 2003.
U.S. Office Action for Tong Sun Wing, U.S. Appl. No. 09/997,059, filed Nov. 29, 2001, dated Nov. 13, 2003.

*Primary Examiner*—Frank W Lu
(74) *Attorney, Agent, or Firm*—Law Offices of Albert Wai-Kit Chan, PLLC

(57) ABSTRACT

The presence of a nucleic acid target, molecule or ligand can be detected by hybridization, antigen-antibody reaction or receptor-ligand binding. This is reported by the strategic positioning of a first probe and a second probe attached to a small particle of electrical conductor, which closes an electrical circuit, thereby reporting the event. A myriad of potential applications of this technique include the identification and detection of small amounts of nucleic acids by hybridization, the detection of molecules such as toxins and carcinogens by antigen-antibody reaction and the detection of other molecules by receptor-ligand interaction. The method can also be adapted to assay the quantity of a given substance using the principle of competitive binding.

8 Claims, 11 Drawing Sheets

SEQUENCE LISTING

```
<160> NUMBER OF SEQ ID NOS: 8

<210> SEQ ID NO 1
<211> LENGTH: 9
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(9)

<400> SEQUENCE: 1 ctggaagga                                                                  9

<210> SEQ ID NO 2
<211> LENGTH: 23
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(23)

<400> SEQUENCE: 2
ggtggcggct gttgctgctg ctg                                                 23

<210> SEQ ID NO 3
<211> LENGTH: 32
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(32)

<400> SEQUENCE: 3
tccttccagc agcagcagca acagccgcca cc                                       32

<210> SEQ ID NO 4
<211> LENGTH: 32
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(32)

<400> SEQUENCE: 4
aggaaggtcg tcgtcgtcgt tgtcggcggt gg                                       32
```

```
<210> SEQ ID NO 5
<211> LENGTH: 20
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(20)

<400> SEQUENCE: 5
ggtggcggct gttgctgctg                                               20

<210> SEQ ID NO 6
<211> LENGTH: 9
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(9)

<400> SEQUENCE: 6 aggaaggtc                                                           9

<210> SEQ ID NO 7
<211> LENGTH: 20
<212> TYPE: DNA
<213> ORGANISM: Artificial
<220> FEATURE:
<223> OTHER INFORMATION: Synthetic probe

<400> SEQUENCE: 7
gtcgtcgttg tcggcggtgg                                               20

<210> SEQ ID NO 8
<211> LENGTH: 29
<212> TYPE: DNA
<213> ORGANISM: Artificial
<220> FEATURE:
<223> OTHER INFORMATION: Synthetic probe
<220> FEATURE:
<221> NAME/KEY: misc_feature
<222> LOCATION: (1)..(29)

<400> SEQUENCE: 8
ggtggcggct gttgctgctg ctgctgctg                                     29
```

MOLECULAR DETECTION AND ASSAY BY ELECTROBIOCHIP MICRO-ARRAY

The application herein is a continuation-in part of U.S. Ser. No. 10/846,770, filed on May 13, 2004, now abandoned, which is a continuation-in-part of U.S. Ser. No. 09/997,059, filed on Nov. 29, 2001, now abandoned; also claims priority of Application No. 90131646 from Taiwan, Republic of China, filed on Dec. 20, 2001; Chinese Application No. 02152977.9, filed on Nov. 29, 2002 and Application No. 03106602.4 from Hong Kong, China, filed on Sep. 15, 2003, the content of which are incorporated by reference here into this application.

Various references are referred to throughout this application. Disclosures of these publications in their entireties are hereby incorporated by reference into this application to more fully describe the state of the art to which this invention pertains.

The present application includes a Sequence Listing filed herewith on a floppy disk. The Sequence Listing is presented in a single file named sequence.txt, and having 2,082 bytes, the disclosure of which is incorporated herein by reference in its entirety.

FIELD OF THE INVENTION

This invention is widely applicable to medicine, industry—both civilian and defense, environmental monitoring and scientific research. It involves the detection and assay of molecules by virtue of specific binding with other synthetic or natural molecules and the detection thereof.

BACKGROUND OF THE INVENTION

Nucleic acid hybridization, antigen-antibody reaction and receptor-ligand binding are examples of molecular interactions, which because of the specificity of the interaction, are of tremendous value in the identification, or detection of these substances. An example is the detection of biological agents and toxins in food and water by specific antibodies and the detection of nucleic acid sequences specific to certain microorganisms employing hybridization techniques. The ability to specifically detect these substances with or without target amplification techniques (applicable to nucleic acids) permits the identification of the putative agents or substances.

SUMMARY OF THE INVENTION

There is disclosed herein a method of detecting and identifying trace quantities of a molecular target by exploiting a specific interaction between the target and two molecular probes, comprising:
  attaching one of said molecular probes to a conductive bead with magnetic properties,
  fixing the other of said probes in a gap between the two electrodes,
  applying a magnetic field to the device to fix the beads against the electrodes,
  applying an electric potential to said electrodes, and
  monitoring for a reduction in electrical resistance, or an increase in electrical current (conductance) from one of the electrodes to the other as might occur if said conductive bead is drawn into said gap by said specific interaction.

Typically, one of the probes is physically bound to a "well" in between the electrodes. If a target is present, it binds to this probe under the right conditions. The other probe that carries the conductive bead then binds to the other part of the target.

Preferably, the conductive bead is an iron bead (such as naturally occurring within a bacterium Shewanella putrifaciens (Reference 1)). The bead can be made of alternative materials, including any electrical conductor (molecule, polymer, elemental metal or combinations) or semiconductor that also have magnetic properties.

Preferably the conductive bead is demagnetized prior to attachment of said one of the molecular probes.

Preferably, said demagnetization is by heating in an environment shielded from the Earth's and other magnetic field(s).

Fixation or magnetic welding of the ferromagnetic beads to the electrodes and to each other by a burst of strong magnetic field causes a circuit to close.

The specificity of the reaction between the probe and the target is the basis of detection.

In addition, the process can be engineered to detect multiple agents/molecules in a microprocessor-controlled microarray or to assay the concentration of a given substance.

There is further disclosed herein a method of detecting trace quantities of a molecular target by exploiting a specific interaction between the target and two molecular probes, comprising the steps of:
  (a) preparing a specimen by putting a gas or solid into solution or otherwise preparing an agent to be identified,
  (b) introducing the specimen into a detecting device with two closely placed electrodes, in the interval of which are bound probes, and allowing for binding/hybridization to occur,
  (c) before, during or after step (b) adding a second probe (in excess of the target) that is bound to an electrically conductive bead and allowing for specific binding/hybridization to occur, and
  (e) determining if binding of the conductive bead to the gap has occurred by detecting a change in any current between the electrodes.

Preferably, step (c) employs an environment not conducive to rusting of the iron beads, such as prior de-oxygenation of the carrier fluid by heat or by displacement with Nitrogen gas.

Preferably, step (e) is preceded by:
  (d) adjusting chemistry and/or temperature of the solution to optimize reaction conditions.

Preferably step (e) employs the use of a microprocessor.

Preferably step (a) includes physically and/or chemically reducing (breaking) a cell to its components and liberate its contents/components for detection.

The method can be engineered into two or three-dimensional microarrays and used to detect multiple different molecules of different chemical nature, including but not limited to nucleic acids, proteins, carbohydrates, lipids and inorganic molecules.

The method can include built-in duplications or triplications for quality control.

The method can also include an electronic self-check and/or pre-analytic test run with negative controls.

The method can also include a post-analytic test run with positive controls should the test result be negative.

There is still further disclosed herein a method for assaying the concentration of a given substance in solution, comprising:
  providing an array of individual chips, each comprising a closed electrical circuit including probes-bound analyte and conductive beads between a pair of electrodes, wherein the chips differ in the size of the gap between the electrodes and the quantity of bound analyte and hence quantity of said beads, introducing a sample containing an unknown concentration of analyte to the microarray, whereby the analyte displaces the bead-bound probes competitively in chips containing a given amount or less of bound analyte but not those containing a larger amount of bound analyte, and chips that have sufficient beads displaced will be converted to an open circuit.

Preferably prior calibration with standards of known concentrations permits the assay of the concentration of analyte in the sample.

There is yet still further disclosed a method of assaying the concentration of a substance by providing less "well"-bound probes than analyte which outnumber bead-bound probes and allowing the reaction to take place in a microarray of multiple chips without prior bound beads (off). The integrated proportion of chips turned on after the addition of the analyte can be used to calculate the concentration of the analyte. This rendition has the advantage over the prior method when the analyte is either impossible to or too expensive to purify or manufacture for use in the electrobiochip using the prior method.

This rendition comprises:

providing an array of identical chips, with a small gap between two electrodes that accept only one conducting bead each and with well-bound probes, introducing a sample containing an unknown quantity of analyte to the microarray within a cassette that contains known amounts of added bead-bound probes in lesser quantity than the analyte in the sample, whereby a free analyte competes with analyte-bound bead-bound probes (formed after introduced analyte react with bead-bound probes inside the cassette) for binding with said well-bound probes on a limited number of said electrobiochips.

Preferably, the method comprises computation of a concentration of the analyte in the sample using prior knowledge of the amount of bead-bound probe, the proportion of "one" to "off" signals registered by the microprocessor and prior calibration with standards of known concentrations of analyte.

There is still further disclosed herein apparatus for detecting trace quantities of a molecular target by exploiting a specific interaction between the target and two molecular probes, comprising:

a well having two electrodes spaced apart to form a wedge-shaped gap and one of said probes attached to the well, means for applying an electric potential to said electrodes, and means for monitoring for an increase in electrical current from one of the electrodes to the other as might occur if a conductive bead having the other of said molecular probes attached thereto is drawn into said gap by said specific interaction.

Preferably the apparatus is housed with a plurality of other identical apparatus in micro-arrays thereof.

Preferably, the micro-arrays are housed within a cassette.

Preferably, the above is found within a portable device constructed with a slot that accepts the cassette.

Preferably the combination further includes a microprocessor that reads the contents of the cassette from an identifier on the cassette.

DETAILED DESCRIPTION OF THE INVENTION

Explained in detail below, this invention takes advantage of the shape of the gap between the electrodes and the conversion of electrical energy to magnetic energy and hence to kinetic energy of conducting magnetic beads in the establishment of good electrical contact across a previously open electrical circuit.

An open electrical circuit does not conduct electricity. Positioning a conductor across the gap of such a circuit might permit electricity to pass, thereby closing the circuit. However, the contact between the components needs to be sufficiently good in order for resistance to be overcome by the voltage gradient across such contact points. A poor electrical contact will require massive voltage for electricity to pass. Ordinary electrical switches employ springs to abruptly bring the components into contact. This impacting of the two components brought about by the spring, together with other necessary features, such as cleanliness of the junction, and fitting surfaces, ensures good contact and the passage of electricity with minimal resistance, minimum waste of energy, and reduced production of heat.

At the microscopic scale, metals across such contacts form metallic bonds, accounting for the above-mentioned phenomenon. As mentioned, this phenomenon is weak if the metallic components are simply placed adjacent to each other. This may explain why Mirkin needed elaborate maneuvers to achieve electrical conductivity even when gold nanoparticles are positioned between an electrical gap (see articles published in Science: Science Vol 295, Issue 5559, 1503-1506, 22 Feb. 2002; and Science Vol 295, Issue 5559, 1447, 22 Feb. 2002).

In fact, sufficient pressure applied to two metallic components can achieve a permanent bonding-welding. Durand (U.S. Pat. Nos.: 6,104,012; 5,966,813; 6,234,375) and Yablochnikov (U.S. Pat. No.: 5,981,921) teach the application of magnetic impulse welding in the molecular bonding of vehicle frame components.

In this invention, the electrodes are refined to take the shape of an open wedge. This not only facilitates the entry of the bead into the gap, which has a wide mouth and a narrow bottom, but also enables tight wedging of the beads into the gap when force is applied to the beads in the direction of the gap.

The other enabling component is the electrical conductivity of the magnetic beads themselves. Electricity is conducted from one electrode through the beads to the other electrode. Most paramagnetic beads used in the biotechnology industry are coated by plastic and are non-conductors (U.S. Pat. No.: 5,385,707).

The use of magnetism in molecular biology is extensive. Paramagnetic beads are used routinely to facilitate the isolation of nucleic acid molecules and cells from complex solutions. Such beads bound to target molecules are drawn to the side of the test tube to facilitate removal of unwanted material by vigorous washing, testifying to the strength of magnetic force in retaining the beads (U.S. Pat. No.: 6,569,647; Science, Vol 301, Issue 5641, 1884-1886, 26 Sep. 2003).

According to the present invention, the kinetic energy of the beads at the time of impact with the electrodes across the gap is considered important to the quality of electrical contact. When "slinging" a projectile, a few revolutions are required to accelerate the projectile before letting it loose. In one embodiment of this invention, therefore, the beads are "shot" at the wells with sufficient energy for welding to take place, or at least tight impacting at the wedge, between the beads and the two electrodes. To achieve this, after the hybridization or antigen-antibody reactions, the beads are suspended from the inverted electrobiochip (well on top and beads at bottom) under the effects of gravitational force by the specific target molecule and the bound probe pair. This gives the necessary "play" for the beads to gain velocity when accelerated by the magnetic field.

The strength of the covalent bonds in the DNA molecule and the hydrogen bonds between target and probes are sufficient to keep the beads suspended to the well. The shear forces acting on dendrimers during washing can be compared with the magnitude of gravitational forces on the beads.

The number of nucleotides in the DNA molecule determines it length. A DNA molecule of 1 kbase length (1,000 bases) measures approximately 0.33 micrometers in length. If the combined length of the hybridized target and the two molecular probes are 1 kbase from one end of a probe to the other end of the other probe, then the bead will be 0.33 micrometers from the base of the well when suspended. Thus, depending on the design of the probes and the size of the target, the beads will be suspended at a certain predetermined distance from the gap.

The application of a strong magnetic force to the beads directed from the base of the well will accelerate the beads towards the well. Having inverted the well and thereby draining all samples and reagents, the beads will encounter minimal resistance (from the intervening air) during their "flight" to the well. Inverting the well also removes unbound beads, which might otherwise constitute background noise, as well as contaminants, which might adversely affect the bonding or electrical contact between beads and electrodes.

Newton's second law states that acceleration is directly proportional to the applied force and inversely proportional to the mass of the object (F=ma). The velocity of impact depends on the time the beads travel (change in velocity=acceleration×time). The velocity in turn determines the momentum and kinetic energy of the bead (momentum=mass×velocity; kinetic energy=0.5×mass×velocity$^2$).

The momentum, or kinetic energy of the beads at the time of impact with the electrodes, determines whether the wedging is tight and hence the degree of electrical contact. The longer the duration of time of flight, the higher the kinetic energy of the beads. In simple terms, the longer the duration of energy transfer to the beads, the more energetic they are. This energy (kinetic) of the beads is transferred to them by the magnetic field, which in turn is converted by a solenoid from electrical energy stored in a capacitor. The use of an electromagnetic coil and capacitor in this connection is also described in U.S. Pat. No. 6,234,375.

This invention therefore provides a simple solution to the problem of electrical contact addressed by Mirkin, who discloses the use of a much slower method of silver depositing that is also very labor intensive, because it involves multiple washes over a long period of time.

DEFINITIONS

As used herein, the following terms are intended to have the following general meanings:

"Nucleic acid" means DNA, RNA, single-stranded or double-stranded and any chemical modifications thereof. Modifications include, but are not limited to, those which provide other chemical groups.

"Ligand" refers to a molecule that binds to a receptor specifically and thereby induce a signal in the cell, e.g. a hormone is a ligand which when bound to a receptor triggers a cascade of cellular response leading to growth of the cell or other responses.

"Hybridization" used in this document means fusion of two single complementary DNA strands (DNA/DNA hybridization), or the fusion of complementary DNA and RNA strands (DNA/RNA hybridization).

"Analyte" refers to a substance present in the blood or body fluids of a patient. The concentration of an analyte typically varies with metabolic or pathologic states and is of information to clinicians managing a given patient's health.

"Antigen" means a substance with a molecular surface structure that triggers an immune response, i.e., the production of antibodies, and/or that reacts with (its) specific antibodies (antigen-antibody reaction). "Antibody" is a protein (immunoglobulin) that recognizes and binds to an antigen as part of the immune response.

"Molecular probe" means any molecules of nucleic acids, proteins or other molecules that have the property of specifically binding to another molecule of the same or a different class. Generally, nucleic acids bind specifically to nuclei acid showing sequence complementarity. Thus, a probe (in this case a nucleic acid molecule) with the following sequence of A-G-G-C-G-T-A (from 5' to 3' end) will bind specifically with another strand of DNA containing a region with the following sequence of T-A-C-G-C-C-T (from 5' to 3' end), where A, T, G and C stand for adenine, thymine, guanine and cytosine, respectively. An antibody to an antigen can be used as a molecular probe against that antigen.

"Epitope" refers to the part of an antigen molecule that binds to an antibody. An antigen can have many different epitopes, which bind to different antibodies. "Electrically conducting magnetic beads" refers to any substance with inducible magnetic property that is also a conductor of electrical current; either an intrinsic property of the material (such as ferromagnetic or paramagnetic material) or a result of engineering, such as electroplating an insulator with magnetic property (for example, ferrimagnetic material), alloying with other metals or building a composite material out of various materials.

"Microsatellite" refers to small run (usually less than 0.1 kb) of tandem repeats of a very simple DNA sequence, usually 1-4 bp, for example $(CA)_n$.

"Microsatellite instability" refers to a phenomenon characteristic of certain tumor cells, where during DNA replication the repeat copy number of microsatellites is subject to random changes.

BRIEF DESCRIPTION OF THE DRAWINGS

Preferred forms of the present invention will now be described by way of example with reference to the accompanying drawings, wherein.

DESCRIPTION OF THE PREFERRED EMBODIMENTS

Figure 1:
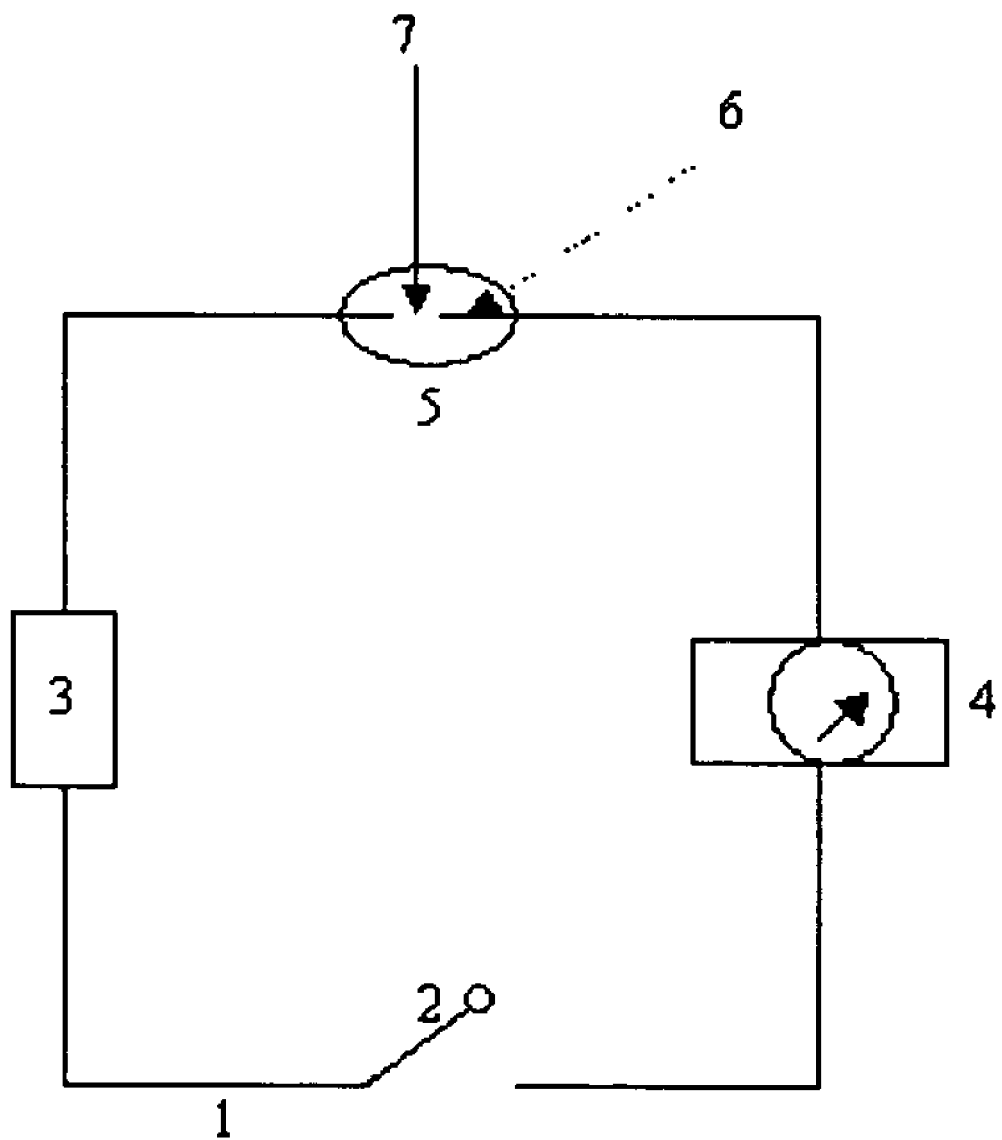
FIG. 1 is a schematic diagram of a circuit employed in a test apparatus.

In FIG. 1 the basic unit comprises the conducting wires 1, a switch 2, a battery 3, a multimeter, galvanometer or microprocessor 4, and the reaction "well" 5 containing the two electrodes 6 with a small gap 7 between them. The circuit is open but when iron beads are positioned between the electrodes, then turning on the switch 2 completes the circuit and results in the flow of an electrical current, which is detected by the multimeter 4.

Figure 2:
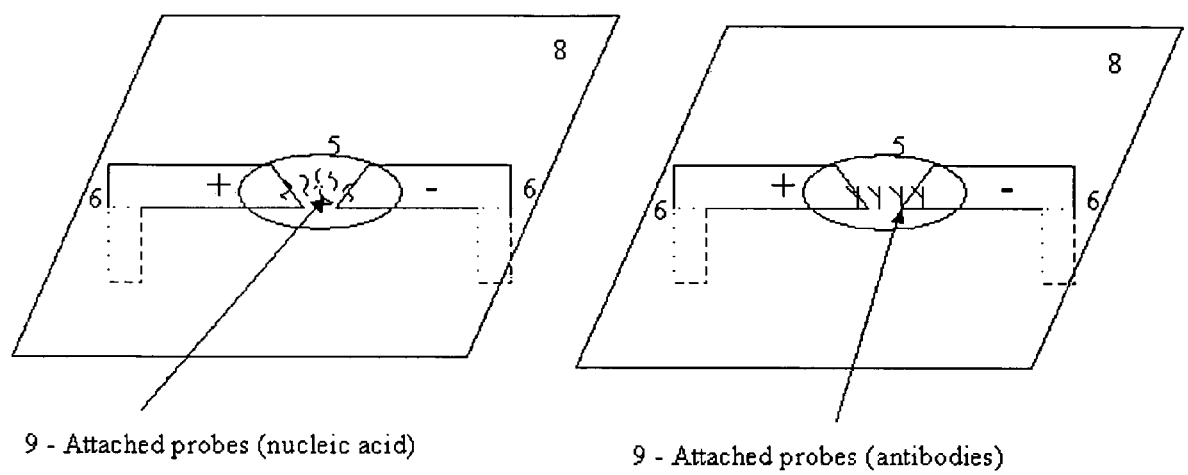
FIG. 2 shows schematic representations of two chips with attached probes and attached antibodies, respectively, FIG. 3 schematically depicts the addition of the second probe with bound iron beads, FIG. 4 schematically depicts one possible micro-array design, FIG. 5 schematically depicts the principles behind one method of quantification of an analyte, FIG. 6 schematically depicts quantification of an analyte using a microarray containing previously bound beads with sandwiched target between probes, FIG. 7 schematically depicts the principles of another method of quantification of an analyte employing competitive binding without previously bound beads, and FIG. 8 schematically depicts the second method of quantification of an analyte using a microarray in the presence of excess analyte.

In FIG. 2 the chip 8 is the reaction "well" plus electrodes alluded to in FIG. 1. In the center of the chip is a "well" 5 which may be a small depression, to the walls of which are covalently bound molecular probes 9 specific for the molecule (target) being sought/assayed. The probes can be nucleic acid (left panel) or antibodies (right panel). Against either wall of the "well" are the two electrodes 6 which slope to the bottom of the well, giving a "wedge-shaped" appearance when viewed from the side or on cross-section. The "well" does not have to be depressed when multiple chips are fabricated into a micro-array (see FIG. 4). The advantage of having a flat "well" is easier removal of unbound excess iron bead-bound probes (described in FIG. 3) at the end of the reaction by the application of a magnetic field.

Figure 3:
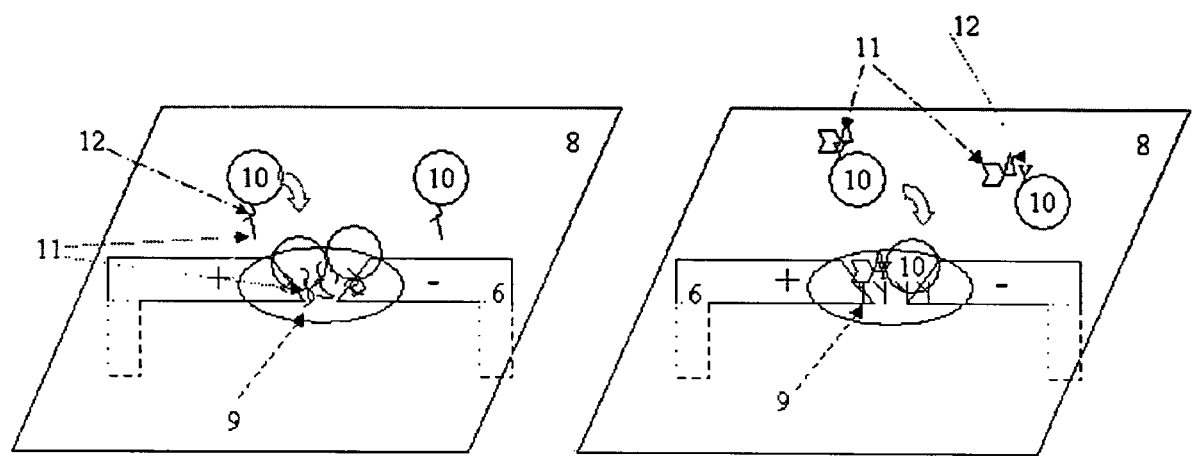

In FIG. 3 some electrically conductive beads such as iron beads 10 are depicted between the two electrodes 6, bound by the sandwiched target molecule 11, which is attached to the "well"-bound first probe 9 and the iron bead-bound second probe 12. In the left panel, the probes are nuclei acid molecules recognizing different portions of the target nucleic acid. In the right panel, the probes are antibodies specific for different regions (epitopes) of the analyte, usually a protein molecule.

Figure 4:
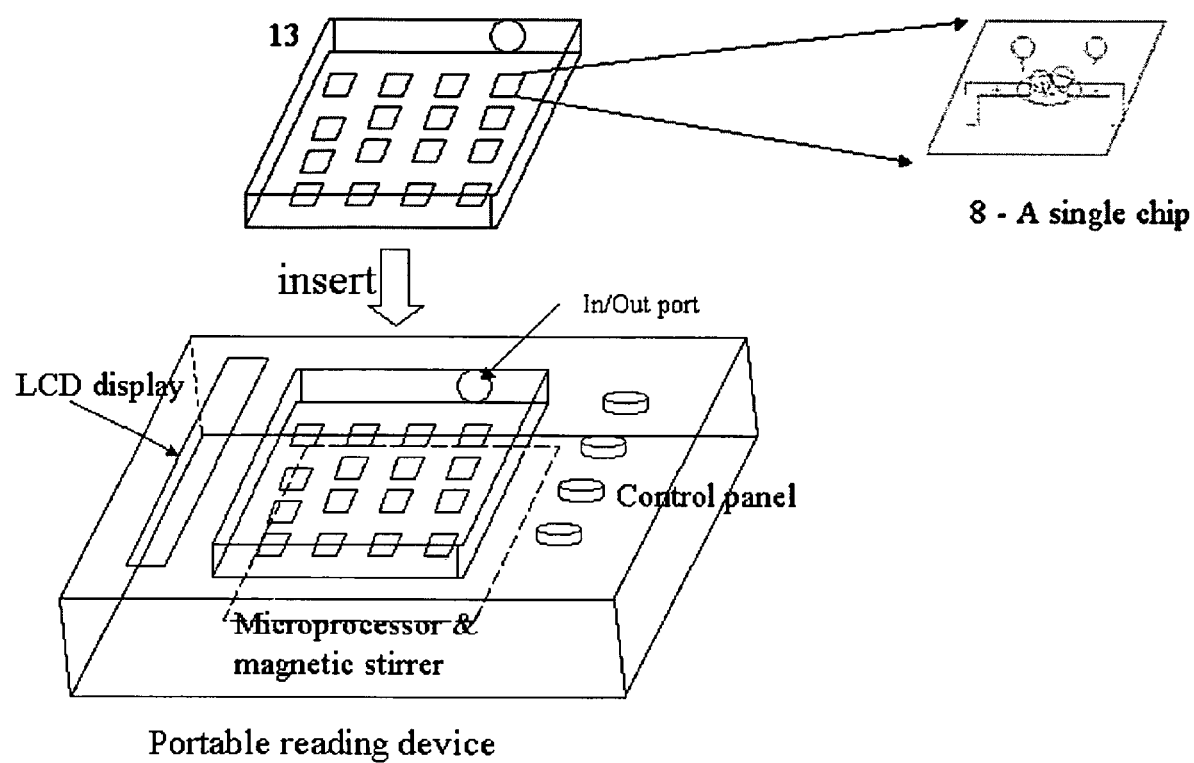

In FIG. 4 the chips are miniaturized 8 and each is designed to detect a specific molecule different from the rest. In and out ports enable introduction of reagents and samples into the chip. In this way, and with the computational power of a microprocessor, multiple agents/molecules can be detected at the same time (multiplex) on one portable device. The cartridge 13 bearing the micro-array is disposable and can be changed to another one or a different one measuring a different set of molecules. Duplications or triplications can be built in for quality assurance. Also, a pre-run with a negative control and a post-run (if the test result was negative) with positive control assures of the accuracy of the test.

Figure 5:
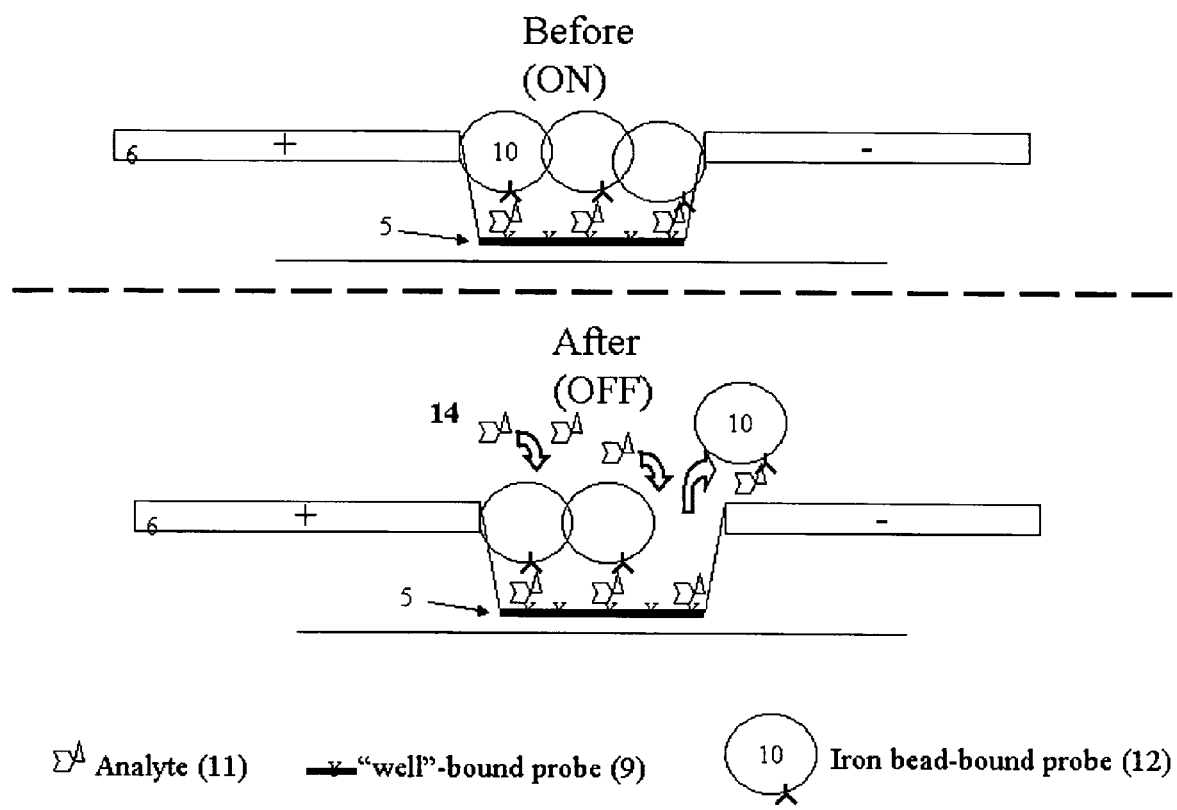

In FIG. 5 the analyte 11 is sandwiched in the test "well" 5 between the two probes, one 9 bound to the "well" and the other 12 bound to iron beads 10 which are in contact (on) with the electrodes 6. Addition of the test sample 14 with sufficient concentration of the analyte causes competitive binding and displacement of the second probe with its attached iron bead, thus breaking the circuit (off).

Figure 6:
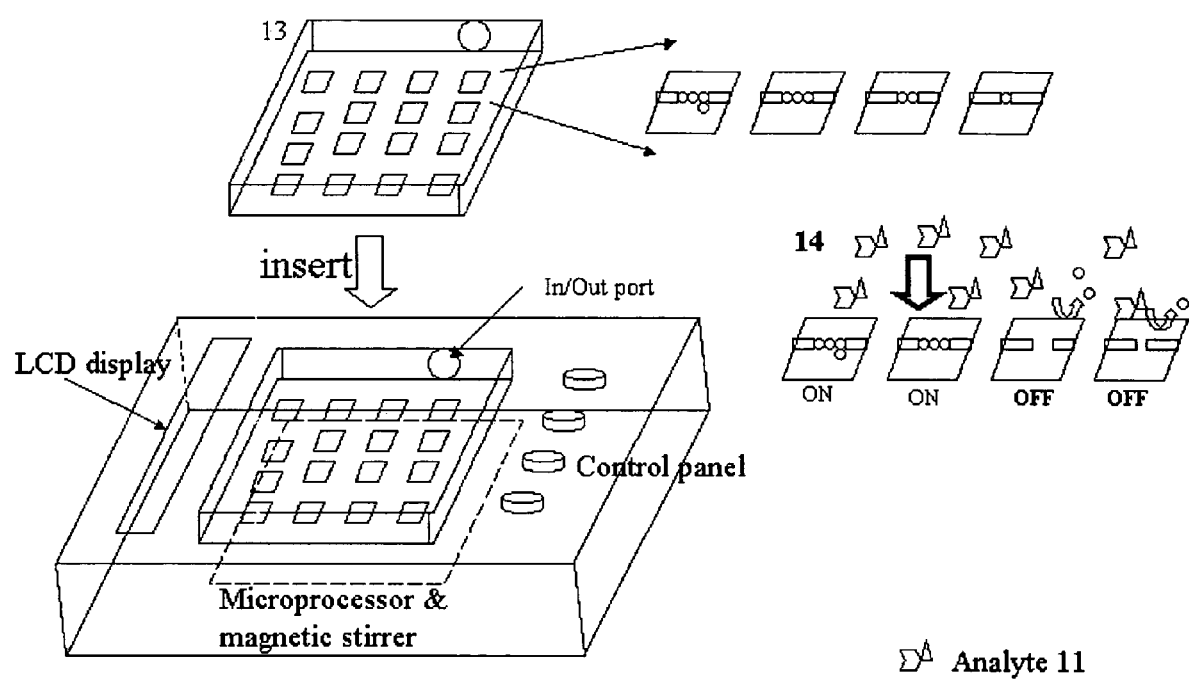

In FIG. 6 the amount of sandwiched analyte and iron beads between the electrodes is gradually varied in a series of chips fashioned into an array to permit determination of the unknown concentration of an analyte as explained below.

Figure 7:
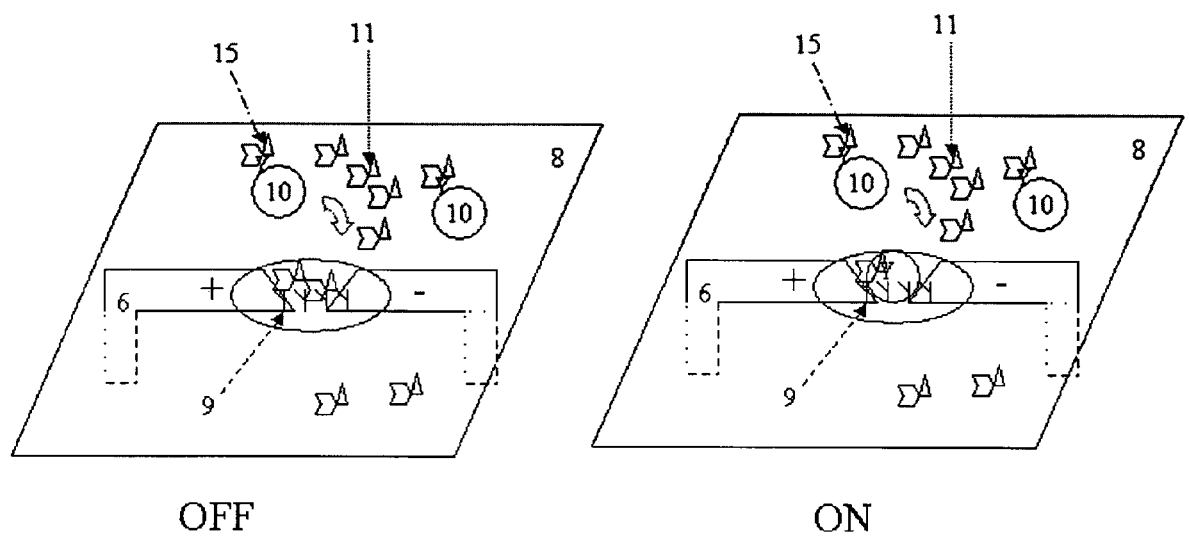

In FIG. 7 no previously bound beads are used. Bead-bound probes. are present in smaller quantity than the analyte. The result is analyte-bound-bead-bound probe 15 compete with free analyte 11 for binding with limited "well"-bound probes 9. The gap between the electrodes is narrowed to admit only one bead. The left panel shows "well"-bound probes completely occupied by analyte without attached bead-bound probe (off). The right panel shows a bead-bound probe binding an analyte molecule attached to the "well"-bound probe (on).

Figure 8:
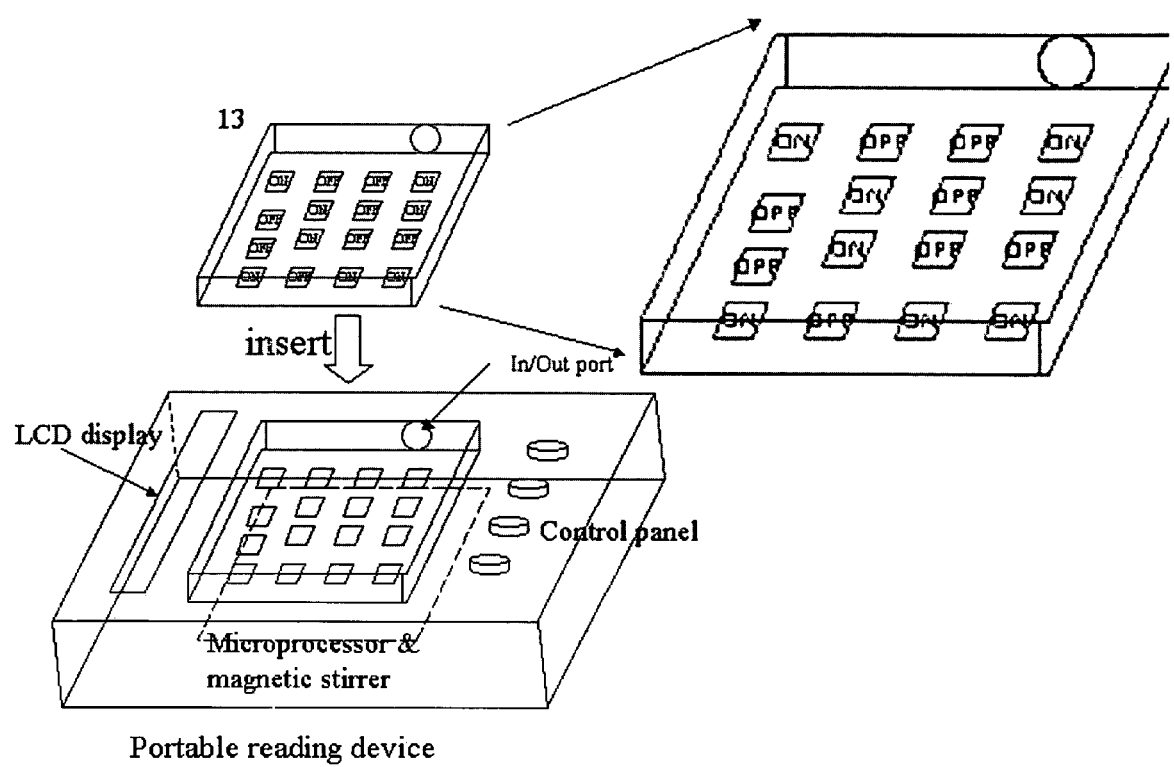

In FIG. 8 a microarray of a multitude of these chips register the total number of "on" signals as a result of binding of analyte-bound-bead-bound probes to the "well"-bound probe. The chips which "well"-bound probes are occupied by free analyte unattached to bead-bound probes will register an "off" signal. The proportion of "on" to "off" signals is determined by the relative concentration of analyte-bound-beadbound probe and free analyte. The magnified view of the cartridge 13 shows that some chips are turned on while others are off. Prior knowledge of the molar concentration of the bead-bound probe permits computation of the concentration of the analyte.

Figure 9:
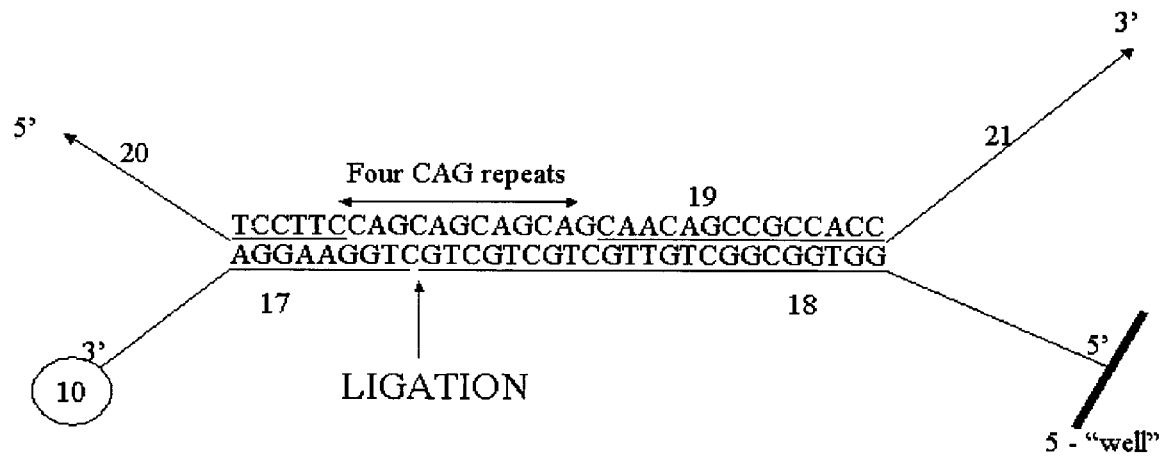
FIG. 9 schematically depicts the design of probe 17 (SEQ ID NO:1) and probe 18 (SEQ ID NO:2) for the repeat region of the Huntingtin gene. The top strand 19 (SEQ ID NO:3) is the target gene bearing four sets of CAG repeats.

In FIG. 9 the principles of measuring the number of CAG repeats in Huntington's disease is illustrated. Description of the method is found in EXAMPLE 9. The bead bound probe 17 is designed to have the following sequence in the probing region: CTGGAAGGA (SEQ ID NO:1) and the "well"-bound probe 18 the following sequence in the probing region: GGTGGCGGCTGTTGCTGCTGCTG (SEQ ID NO:2). In the drawing, the top strand 19 is the target gene bearing four sets of "CAG" repeats in this particular patient. Only the regions complementary to the probes are depicted with the actual nucleotide sequence. The other ends (5' 20 and 3' 21) are represented by arrows. The hybridized bead-bound 17 and "well"-bound probes 18 are depicted using the same convention. The underlined parts of the probes (above the drawing) highlight the non-repeating portion flanking the repeat areas. In the drawing, the two probes have a combined number of repeats matching that of the target (four to be exact). Thus the 5' and 3' ends of these probes are brought together and can be ligated by an enzyme (DNA ligase).

Figure 10:
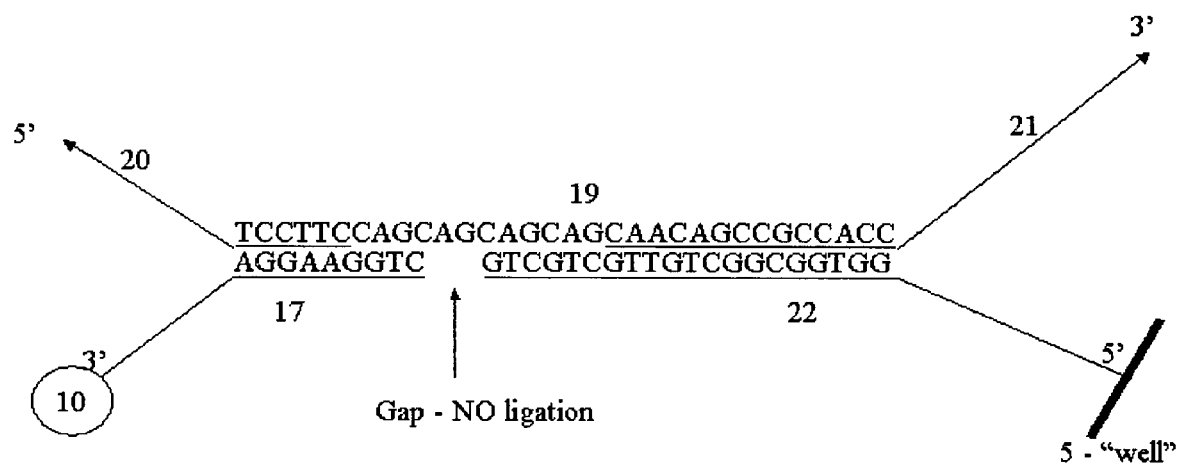
FIG. 10 schematically depicts another set of probes: probe 17 (SEQ ID NO:6, 3' to 5') and probe 22 (SEQ ID NO:5) that have a combined number of repeats that fall short of the exact number of repeats present in a given patient. No ligation of the two ends of the probes occurs. The top strand 19 (SEQ ID NO:3) is the target gene bearing four sets of CAG repeats.

In FIG. 10 only the sequence of a different "well"-bound probe 22 is illustrated as the bead-bound probe is the same. This "well"-bound probe 22 is placed on another electrobiochip on the same microarray. The "well"-bound probe 22 illustrated here has only two repeats, causing a gap to be present between the two probes upon hybridization with the target. The two probes cannot be ligated.

Figure 11:
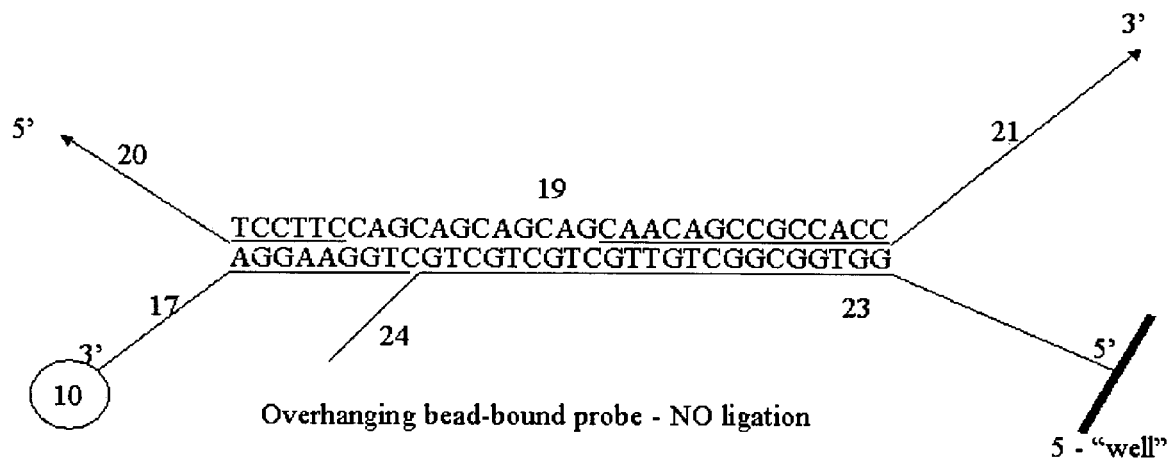
FIG. 11 schematically depicts yet another set of probes: probe 17 (SEQ ID NO: 6, 3' to 5') and probe 23 (SEQ ID NO:8) having a combined number of repeats in excess of the exact number of repeats present in a given patient, giving rise to overhanging probes and failure of ligation. The top strand 19 (SEQ ID NO:3) is the target gene bearing four sets of CAG repeats.

In FIG. 11 yet another "well"-bound probe 23 has too many repeats (5 in number). The excess portion therefore "overhangs" 24 after hybridization. Again there is no ligation.

Specimen Procurement

Air containing a putative target can be bubbled through a suitable solute. Solid or liquid can be dissolved in solution. Intact cells and tissue require to be broken open or otherwise prepared to liberate the molecule being detected.

The Device (Electrobiochip)

In its simplest designs, the electrobiochip (chip) consists of a small test "well" that contains two electrical wires inside, with a small gap between them. The electrodes are shaped in such a way that the space between the two electrodes is shaped like a wedge when seen from the side, with the base of the wedge on top. In the gap between the electrodes are bound molecular probes that are specific for the putative target. The other component is a second specific probe that is bound to small beads of electrical conductor with magnetic properties, such as iron beads.

The Reaction

The sample is added to the chip. The second probe is added in excess of the target (prior to, during, or after the addition of the sample). Reaction is allowed to happen. After the reaction, unbound probes and iron beads are drawn aside by generating an adequate magnetic field or inversion and drainage of the chip. A magnetic field is then generated preferably at the base of the device, fixing bound electrically conductive magnetic beads firmly in the wedge-shaped space between the electrodes. This step is important as it ensures adequate electrical contact between the beads and the electrodes. Finally, the conductance/resistivity is measured and the result is recorded.

Quantification

The width of the gap between the two electrodes and the amount of "well"-bound probes and hence sandwiched "well"-bound-probe/target/bead-bound-probe can be varied in an inversely engineered (recording "off"-signal rather than "on"-signal) array of chips to measure the amount (competitiveness) of target present within a test sample. Addition of a test sample containing target only results in competitive binding and displacement of bead-bound-probes. Only those chips containing more than a certain amount of sandwiched "well"-bound-probe/target/bead-bound-probe remain "on". Other chips are turned "off" because of competitive binding and displacement of the bead-bound-probes by the added analyte. Prior calibration with known standards permits accurate quantification of the test sample.

Yet another method of quantification involves measuring in a microarray with multiple chips, the number of previously "off" chips (without prior bound beads with sandwiched target (between two probes)) that are turned "on" in the presence of an unknown concentration of the analyte present in excess of the bead-bound probe.

Creation of Molecular Probes

A pair of specific molecular probes is first created. Nuclei acid probes can be constructed with knowledge of the sequence of the target. Such sequence information can often be found in databases such as Entrez-Genome (National Center for Biotechnology Information, National Library of Medicine, National Institutes of Health, USA). Probes with sequences complementary to the two ends of the target can be synthesized commercially. In addition, probes can be designed in such a way that upon hybridization with the target, the two ends of the probes are brought into physical proximity such that a DNA-ligase (an enzyme that covalently joins DNA strands that are brought together) can ligate the two ends to strengthen the bond between iron beads and "well".

Antibodies can be produced from laboratory animals exposed to the antigen. Because of that, a source of antigen is required.

Layout of a Single Electrobiochip

Nucleic acid probes or antibodies can be bound covalently to various materials. The first probe is bound to the wall of the container along a small gap between the two ends of an open electrical circuit (FIGS. 1 & 2). The two electrodes are connected by conducting wires on the chip to a microprocessor that forms and/or monitors the rest of the circuit. A second specific probe is bound by similar techniques to tiny free iron beads which may be obtained in nature from iron-reducing bacteria such as Shewanella putrifaciens. When a target is present and under the right conditions, it is bound to and sandwiched between the two probes (FIG. 3). By virtue of the location of the first probe, the iron bead bound to the second probe is brought into contiguity with the electrodes and with the help of a magnetic field and special shape of the electrodes, closes the electrical circuit, permitting the passage of an electrical current when a battery supplies the potential difference. The range of concentration of the target is extremely wide, from one single molecule to as many as there are bead bound-probes, providing for robustness of design. Yet, the sensitivity is not compromised. This setup can theoretically detect the presence of only one molecule. In addition, when used for the detection of specific nucleic acid sequences, no prior amplification is necessary. This method is versatile and can be used to detect DNA, RNA, proteins, and other macromolecules.

Fabrication of a Micro-array

Multiple single chips can be fabricated into a micro-array (FIG. 4). These individual chips can be made to detect different molecules. Duplications or triplications of the same chip can be made on the same microarray for quality assurance purposes.

The second probes with the bound iron beads are housed in the cassette containing the microarray. A slight vacuum is engineered in the cassette (which has a part that can balloon a little to accept some more sample) in order to draw in a predetermined volume of sample. The in/out port in the cassette permits introduction of the sample into the cassette.

Reading Device

A portable device is constructed which has a slot that accepts the cassette. Inserting the cassette connects the many small circuits (FIG. 4) on the bottom (or side) of the cassette with the microprocessor through the electronics of the reading device. The microprocessor reads the contents of the cassette from a unique identifier such as a bar-code at the bottom of the cassette and programs itself to interpret the on/off signals and display the result as "biological agents" detected or to report on the "concentration" of the analyte.

Thus, to "read" the result, the cassette is inserted into the device. The electrical circuits of the microarray are then in contact with the electronics of the microprocessor housed in the reading device. The microprocessor optimizes the reaction temperature, times the reaction, and controls an array of tiny solenoids that produce a varying magnetic field to achieve the effect of gentle agitation of the reactants to facilitate the reaction. At the end of the reaction, the microprocessor generates a perpendicular (to the axis of the electrodes) magnetic field, which draws away unreacted iron bead-bound probes to remove spurious signals. The electrodes should be made of copper or other electrically conducting material that is not inducible by magnetic fields. The microprocessor then interprets the on/off signals registered from the individual chips of the microarray and generates the result as a text display on the liquid crystal display (LCD), Braille or synthetic voice. The buttons on the control panel permit the operator to navigate the menus and perform various functions as necessary. The result can also be transmitted by radio to a remote location or printed out on a pre-configured printer. For more sophisticated designs, the complicated electronics might dictate that the microprocessor be built into the disposable cassette. Alternatively, the entire device can be disposable after reuse for a specified lifetime with the test chamber being washed and re-filled (with bead bound-probes, reagents and carrier fluid) in between each use.

Molecular Assay

Known biological molecules in body fluids often need to be assayed for the concentration. An example is the assay of thyroid hormones in thyrotoxic or hypothyroid states.

The principles of this invention permit a point-of-care assay by the bedside or in the clinic using a tiny sample of body fluid or blood in a timely fashion and without the use of room-filling complicated machinery. The chip (basic unit) is designed to carry the sandwiched analyte specifically attached to the "well"-bound probe and iron bead-bound probe in sufficient quantity to close the gap between the two electrodes. In this configuration, the circuit is always "on" unless iron bead-bound probes are displaced.

Iron bead-bound probes can be displaced when sufficient concentration of unbound analyte is added to the chip. This is achieved because the unbound analyte competes with bound analyte for iron bead-bound probe or "well"-bound probe, causing the previously aligned iron bead of the circuit to be displaced. The result is now an open circuit (off). A microarray can be fabricated, on which are multiple chips, each varying slightly by the width of the gap between the two electrodes and the amount of aligned sandwiched analyte/iron bead-bound probes. The addition of an unknown amount of analyte results in some iron bead-bound probes being displaced. While this will not affect those chips with a wider gap and more iron bead-bound probes (remaining "on"), those with lesser gap and smaller numbers of iron bead-bound probes will be turned off. The position between a series of "on" chips and a series of "off" chips gives an accurate estimate of the concentration of the analyte in the test material. Displaced beads are drawn aside by a magnetic field before reading. Prior calibration with standards with known concentrations is required. This method is satisfactory when nucleic acid is being measured because of the ease of synthesizing nucleic acid targets in the laboratory.

When it is too difficult or expensive to purify or synthesize an analyte (e.g. proteins or other macromolecules) for the purpose of making the prior electrobiochip, it is still possible to use this invention to assay the concentration of an analyte in a body fluid or blood.

A microarray containing multiple electrobiochips are made, with each chip containing "well"-bound probes. These probes are likely to be antibodies, but can also be nucleic acids (especially when viral load is being assayed). A different probe is made which is bound to conducting beads. Smaller quantities (mole for mole) of the second bead-bound probe are used in the presence of the analyte. By competition for the multiple but still relatively much fewer (compared with free and bead-bound probe-bound analyte) chips, and with knowledge of the amount of bead-bound probes used, the concentration of the analyte can be computed by the proportion of chips turned on, as measured by the microprocessor. The large number of electrobiochips in the microarray is necessary to give an accurate result. The chips are also made to accept only one electrically conducting bead to enhance accuracy. In order that the dynamic equilibrium is not disturbed, bead-bound probes unattached to the "well"-bound probes are not drawn aside by a magnetic field. A series of measurements are taken and averaged to give a final result.

EXAMPLES

Example One

The ribosomal ribonucleic acid (rRNA) of Mycobacterium tuberculosis (the cause of human tuberculosis) is the target of detection in the AMPLIFIED™ Mycobacterium Tuberculosis Direct Test (References 2-11). Whereas amplification is required in the above test (Transcription Mediated Amplification (TMA)), the current invention requires the simple process of breakdown of the bacterial cell wall to liberate the rRNA.

Using our electrobiochip, as little as one copy of the bacterial rRNA can be detected. No prior amplification is necessary.

Example Two

The timely laboratory diagnosis of an acute myocardial infarction (heart attack) is potentially lifesaving because therapeutic interventions can be instituted. These interventions are not without their own risks and mandate an accurate test.

Until now, tests are either not sensitive enough or non-specific. For example, the earliest indicator of myocardial infarction is elevation of serum myoglobin, which is detectable at 6 hours after infarction (References 12-15). However, myoglobin is also present in skeletal muscle and its elevation is not specific for myocardial injury, requiring confirmation by a second assay of serum troponin T, a marker that is elevated later than myoglobin.

The ability to detect minute quantities of cardiac troponin T in the earliest stages of an acute myocardial infarction requires both specificity and sensitivity. This is now possible using our electrobiochip.

In this application, the principle of competitive binding is employed as described in "QUANTIFICATION" above. The analyte would be cardiac troponin T and the two probes would be antibodies raised against cardiac troponin T. The antibodies should bind to two different epitopes on the cardiac troponin T molecule with avidity and without interference of each other (epitopes not too close as to interfere with the binding of the two antibodies). In addition to being able to detect previously undetectable quantities of circulating cardiac troponin T early in an episode of acute myocardial infarction (which probably exists much sooner than 6 hours after an acute myocardial infarction), the application also permits quantitation of the serum level of this protein (calibration of the instrument can be readily achieved by serial dilutions of known concentrations of cardiac troponin T).

Example Three

In scientific research, scientists frequently need to study gene expression. In a multicellular organism, cells carrying the same set of genes specialize to takes up numerous bodily functions such as covering the body surface (integument or skin), absorbing fluids and electrolytes (intestines), and interacting with the outside world (nervous system). As the result, the cells need tools which are expressed in these specialized cells that are not expressed in the other differentiated cells. Until now, gene expression is studied by fluorescent probes or other means, individually or employing the recently much discussed microarray, on which are printed or otherwise attached molecular probes which hybridizes with the messenger RNA and create a qualitative result of present or absent. Needless to say, these microarrays do not have the ability to quantitate the mRNA, which may be expressed but at a low level. Low level expression may also be important because we do not know that low level expression is necessarily synonymous with few proteins being made because protein concentration in a cell is dynamic and represents an equilibrium between production and destruction.

With this invention, quantitation of mRNA and the corresponding protein is simple, as described in "QUANTTFICATION" above.

Example Four

Mutation detection is a means to discover that a given disease is handed down in the germ cells (hereditary). The detection of single point mutations in genes (sometimes very large) by conventional methods that are based on amplification of areas of genes suffer from the disadvantage that large segments cannot be amplified and hence restricting the ability to economically and systematically studying a given person's gene for point mutations.

With this invention, pairs of probes ("well-bound and bead-bound) can be designed with knowledge of the sequence of unmutated genes (found in public databases). The pair of probes is designed to be complementary to consecutive stretches of the sequence. As many pairs are designed as necessary to cover the entire length of the gene being studied and the different "well"-bound probes attached to individual electrobiochips, the region they are probing being stored in the unique identifier of the cassette.

In this way and with a special construct of the device to make it reusable, fast, economical and systematic study of gene mutation can be performed. The same method can be used to define single nucleotide polymorphisms.

Example Five

Many cancers are caused by the transposition of a portion of one gene to or within another gene (chimeric genes). Examples are too plenty to list and include follicular carcinoma of thyroid, certain acute myeloid leukemias, many soft tissue sarcoma such as synovial sarcoma and extraskeletal myxoid chondrosarcoma.

Whereas identification of the mRNA transcripts (chimeric transcripts) of these chimeric genes are readily performed by conventional polymerase chain reaction for amplification and electrophoresis for identification based on the size of the amplified product, the method is slow and laborious.

Using this invention, a pair of probes can be made that hybridize to the two components of the chimeric transcript. One probe is bound to the "well" and the other is bound to conductive beads. Positive identification can therefore be achieved even with a minute sample harnessed by a fine needle from the tumor or from the blood if the tumor is a leukemia or one that readily enters the blood stream in the early or late course of the disease. Many different cancers can be screened at once in this way.

Example Six

Many diseases have a viral cause. An example is HIV (infection by the human immunodeficiency virus) . Whereas the disease is controllable by anti-viral agents, these are all very expensive. Because the virus is prone to mutation, not all patients are responsive to the same drug(s) at different periods. Monitoring the viral load is one way to determine drug efficacy and disease status.

Using this method, viral load study is rendered highly accurate, simple, fast and economical.

The principles of assay have been previously described. Any virus can be studied using this method, provided the genetic sequence is known.

Example Seven

Many infectious diseases have similar manifestations. For example, anthrax, influenza, dengue fever, smallpox, simple colds, roseola etc. have initial manifestations that include malaise (poor general well-being), fever, muscle aches and non-specific rashes.

In order that primary care doctors can accurately identify these numerous diseases with similar manifestations but hugely different outcomes, this invention can be adapted to detect minute (hence early) quantities of an entire panel of these infectious agents in the clinic, economically and immediately. Many patients do not even need to be hospitalized for observation and can be sent home with positive identification of the cause, saving both money and risks to the patients (if they need to be warded in a hospital which may harbor harmful microorganisms).

Example Eight

Monitoring the drinking water and food (or animal feed) for harmful substances, such as the agent for mad-cow disease (Bovine Spongiform Encephalopathy (BSE)) are hampered by high cost and low sensitivity of the tests (References 16-20). For example, cows with BSE have minute quantities of the agent in their brain fluids (cerebrospinal fluid). A sensitive test can not only detect the disease early but spare the animal from slaughter. Humans who are suspected to have the disease from consumption of diseased cows can also be tested.

Using specific antibodies found by other researchers, this invent -on can tremendously cut the cost and time to identify the causative agent.

Example Nine

Many hereditary diseases are caused by excessive lengthening of certain regions harboring a repetitive sequence. For instance, Huntington's disease, an invariably fatal disease, is caused by the presence of repeats of "CAG" in the Huntingtin gene located in chromosome 4 exceeding thirty six times.

To measure the number of repeats in a person's Huntingtin gene, conventional methods employ PCR. This invention simplifies the measurement of the number of repeats. Thus probes are designed to flank the invariable portions of the gene adjacent to the repeat sequence.

"Well"-bound probes differ in the number of repeats they carry in addition to the in-varying sequence flanking the repeat. The bead bound probes carry the in-varying region on the opposite side of the repeat and one or two repeats. A person with a given number of repeats, e.g. 5 "CAG" repeats will have the two probes perfectly aligned end to end when hybridized if the well-bound probe contains 4 repeats and the bead-bound probe contains 1 repeat. Other "wells" containing "well"-bound probes measuring over 4 (e.g. 5 or more) or less than 4 (e.g. 3 or less) will hybridize but will not produce perfect alignment of the ends. Utilizing a DNA ligase (an enzyme that covalently links two strands of DNA aligned on a complementary strand and with the ends in close proximity), the two probes can be ligated covalently. Probes that have a combined number of repeats more than 5 will have a overhanging strand that is not ligateable with the other strand and so are probes with a combined repeats of less than 5 because of a big gap between the ends of the two probes. After the hybridization and ligation reactions, modification of the reaction conditions causes the probes and target to dissociate (denaturation), resulting in the turning "off" of electrobiochips that have "well"-bound probes having other than exactly 4 CAG repeats.

The result is rapid and accurate measurement of the number of CAG repeats in a person's Huntingtin gene.

This method is adaptable to any of the class of genetic diseases with varying repeat numbers as well as instability in the number of repeats in the inherited or acquired conditions of microsatellite instability.

Example Ten

Proteomics—The proteome of a single celled organism or the proteomes of various cells of a multicellular organism contains over 400,000 proteins. To study the interaction of these proteins among themselves and other molecules is a daunting task.

This invention embodies a method which provides an opportunity to rapidly and economically study protein-protein and protein-other molecule interactions by virtue of specific physical interactions between these molecules. The various proteins of a cell or organism are first isolated and deposited on specific locations on the electrobiochip. Next, each one of these various proteins are bound separately to the surface of an electrically conductive magnetic beads. When the beads are introduced into the electrobiochip in a suitable carrier fluid under suitable thermal conditions, protein-protein interactions can be effortlessly studied in a sequential fashion. In another embodiment, specific antibodies are raised against the entire proteome (for example, of plasma) and specifically addressed onto the biochip. Another set of specific antibodies against alternative epitopes of the proteome is raised. The electrobiochip can then be adapted to measure the quantity of the proteins in a proteome using the principle of competitive binding as outlined above.

Example Eleven

Drug-protein interaction—The first embodiment of EXAMPLE TEN can also be used to study drug interactions with the proteome if drug molecules, rather than proteins, are attached to the electrically conductive magnetic beads.

References

U.S. Patent document 6,234,375 May, 2001 Durand
1. Glassauer S, Langley S, Beveridge T. J. Intracellular iron minerals in a dissimilatory iron-reducing bacterium. Science. 295:117-119.
2. Behr, M. A., S. A. Warren, H. Salamon, P. C. Hopewell, A. Ponce de Leon, C. L. Daley, and P. M. Small. 1999. Transmission of Mycobacterium tuberculosis from patients smear-negative for acid-fast bacilli. Lancet. 353:444-449.
3. Bermann, J. S., G. Yuoh, G. Fish and G. L. Woods. 1999. Clinical evaluation of the enhanced Gen-Probe Amplified Mycobacterium Tuberculosis Direct Test for rapid diagnosis of tuberculosis in prison inmates. J. Clin. Microbiol. 37:1419-1425.
4. Bermann, J. S. and G. L. Woods. 1999. Enhanced mycobacterium tuberculosis direct test for detection of M. tuberculosis complex in positive ESP II broth cultures of nonrespiratory specimens Diag. Microbiol. Infect. Dis. 35: 245-248.
5. Chedore, P. and F. B. Jamieson. 1999. Routine use of the Gen-Probe MTD2 amplification test for detection of Mycobacterium tuberculosis in clinical specimens in a large public health mycobacteriology laboratory. Diag. Microbiol. Infect. Dis. 35: 185-191.
6. Della-Latta, P. and S. Whittier. 1998. Comprehensive evaluation of performance, laboratory application, and clinical usefulness of two direct amplification technologies for the detection of Mycobacterium tuberculosis complex. Am. J. Clin. Pathol. 110:301-310.
7. Della-Latta, P. and Vivian Jonas. 1999. Inhibitory effect of Alpha-Tec XPR-Plus Phosphate Buffer on the enhanced Gen-Probe Amplified Mycobacterium Tuberculosis Direct Test. J. Clin. Microbiol. 37:1234-1235.
8. Gamboa, F., G. Fernandez, E. Padilla, J. M. Manterola, J. lonca, P. J. Cardona, L. Matas, and V. Ausina. 1998. Comparative Evaluation of initial and new versions of the Gen-Probe Amplified Mycobacterium Tuberculosis Direct Test for direct detection of Mycobacterium tuberculosis in respiratory and nonrespiratory specimens. J. Clin. Microbiol. 36:684-689.
9. Moore, D. F. and Curry, J. I. 1999. Reduction in turn-around time for detection and identification of Mycobacterium tuberculosis from pulmonary specimens using nucleic acid amplification tests. Presented at the 99th General Meeting of the American Society of Microbiology. Chicago, Ill.
10. Piersimoni, C., A. Callegaro, C. Scarparo, V. Penati, D. Nista, S. Bornigia, C. Lacchini, M. Scagnelli, G. Santini, and G. De Sio. 1998. Comparative evaluation of the new Gen-Probe Mycobacterium tuberculosis Direct Test and the semiautomated Abbott LCx Mycobacterium tuberculosis assay for direct detection of Mycobacterium tuberculosis complex in respiratory and extrapulmonary specimens. J. Clin. Microbiol. 36:3601-3604.
11. Wang, S. X. and L. Tay. 1999. Evaluation of three nucleic acid amplification methods for direct detection of Mycobacterium tuberculosis complex in respiratory specimens. J. Clin. Microbiol. 37:1932-1934.
12. Bakker A J, Loelemey M J, Gorgels J P, von Vlies B, Smits R, Tijssen J G, Haagen F D: Troponin T and myoglobin at admission: value of early diagnosis of acute myocardial infarction. Eur Heart J 1994.
13. De Winter R J, Koster R W, Sturk A, Sanders G T: Value of myoglobin, troponin T, and CK-MB Mass in ruling out an acute myocardial infarction in the emergency room. Circulation. 1995; 92: 3401-3407.
14. Hamm C W, Katus H A: New biochemical markers for myocardial cell injury. Current Opinion in Cardiology, 1995; 10: 355-360.
15. Tucker J F, Collins R A, Anderson A J, Hess M, Farley I M, Hagemann D A, Harkins H J, Zwicke D: Value of serial myoglobin levels in the early diagnosis of patients admitted for acute myocardial infarction. Ann Emerg Med 1994; 24: 704-708.
16. P. Brown et al., "Bovine spongiform encephalopathy and variant Creutzfeldt-Jakob disease: background, evolution, and current concerns," Emerging Infectious Diseases, 7[1]:6-16, January-February 2001.
17. J. Bieschke et al., "Ultra-sensitive detection of pathological prion protein aggregates by dual-color scanning for intensely fluorescent targets," Proceedings of the National Academy of Sciences (PNAS), 97:5468-73, 2000.
18. M. R. Scott et al., "Identification of a prion protein epitope modulating transmission of bovine spongiform encephalopathy to transgenic mice," PNAS, 94:14279-84, 1997.
19. "The Evaluation of Tests for the Diagnosis of Transmissible Spongiform Encephalopathy in Bovines," European Commission, Directorate General XXIV, Consumer Policy and Consumer Health Protection, Jul. 8, 1999.
20. J. Safar et al., "Eight prion strains have PrPSc molecules with different conformations," Nature Medicine, 4:1157-65, 1998.

What is claimed is:

1. A method of determining the presence of a molecular target in a sample by exploiting specific interactions between the molecular target and two molecular probes, comprising:

attaching a first molecular probe to a conductive bead with magnetic properties and forming a first molecular probe attached to the conductive bead;

fixing a second molecular probe in a gap between two electrodes on a chip, wherein an open electric circuit is formed between the two electrodes;

mixing a molecular target in a sample with the first molecular probe attached to the conductive bead and the second molecular probe, wherein the first molecular probe binds to a first part of the molecular target, the second molecular probe binds a second part of the molecular target and the first and second parts of the molecular target are different such that a complex comprising the molecular target, the first molecular probe attached to the conductive bead and the second molecular probe are formed;

applying a magnetic field to the conductive bead of the complex and fixing the conductive bead of the complex in the gap between the two electrodes;

applying an electric potential to the electrodes; and detecting a flow of electrical current from one of the electrodes to another of the electrodes, wherein the conductive bead fixed in the gap between the two electrodes permits electricity to pass the gap and causes the open circuit to close such that the electrical current flows from said one of the electrodes to said another of the electrodes, therefore the presence of the flow of the electrical current indicates the presence of the molecular target in the sample.

2. The method of claim 1 wherein the gap between the electrodes is located in a well and the second molecular probe is physically bound to the well between the electrodes.

3. The method of claim 1 wherein the conductive bead is an iron bead.

4. The method of claim 1 wherein the conductive bead is demagnetized prior to the attachment of the first molecular probe.

5. A method of determining the presence of a molecular target in a specimen by exploiting specific interactions between the molecular target and two probes, comprising the steps of:
   (a) preparing a specimen comprising the molecular target;
   (b) introducing the specimen to a chip comprising two electrodes that have a between the two electrodes, wherein an open electric circuit is formed between the two electrodes, a first probe is fixed in the gap between the two electrodes, and binds to a first part of the molecular target;
   (c) before, during or after step (b), adding a second probe to the chip, wherein the second probe comprises a conductive bead with magnetic properties and binds to a second part of the molecular target and the first and second parts of the molecular target are different such that a complex comprising the molecular target, the first probe and the second probes are formed;
   (d) fixing the conductive bead of the complex in the gap between the two electrodes by the application of a magnetic field;
   (e) applying an electric potential to the electrodes; and
   (f) detecting a flow of electrical current from one of the electrodes to another of the electrodes, wherein the conductive bead fixed in the gap between the two electrodes permits electricity to pass the gap and causes the open circuit to close such that the electrical current flows from said one of the electrodes to said another of the electrodes, therefore the presence of the flow of the electrical current between the two electrodes indicates the presence of the molecular target in the specimen.

6. The method of claim 5 wherein step (b) or (c) is preceded by adjusting conditions to optimize the binding.

7. The method of claim 5 wherein the specimen is derived from a cell.

8. The method of claim 5 wherein the chip is part of a microarray that comprises a plurality of chips, wherein each of the chips in the microarray can be used to detect the same or different molecular targets.

* * * * *

UNITED STATES PATENT AND TRADEMARK OFFICE
CERTIFICATE OF CORRECTION

PATENT NO. : 7,632,671 B2  Page 1 of 1
APPLICATION NO. : 10/967592
DATED : December 15, 2009
INVENTOR(S) : Sun-Wing Tong It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 565 days.

Signed and Sealed this

Second Day of November, 2010

David J. Kappos
*Director of the United States Patent and Trademark Office*